United States Patent [19]

Depoortere

[11] 4,202,898
[45] May 13, 1980

[54] METHOD OF TREATING ANXIETY AND DEPRESSION

[75] Inventor: Henri Depoortere, Dampierre, France

[73] Assignee: Synthelabo, Paris, France

[21] Appl. No.: 912,738

[22] Filed: Jun. 5, 1978

[51] Int. Cl.² .......................................... A61K 31/495
[52] U.S. Cl. ................................................... 424/250
[58] Field of Search ................ 424/250; 260/268 PH; 544/394

[56] References Cited

U.S. PATENT DOCUMENTS

| | | | |
|---|---|---|---|
| 3,038,901 | 6/1962 | Hayao | 544/394 |
| 3,326,916 | 6/1967 | Creighton et al. | 544/394 |
| 3,557,107 | 1/1971 | Cinnamon et al. | 544/394 |
| 3,953,449 | 4/1976 | Giudicelli et al. | 544/394 |
| 4,031,094 | 6/1977 | Giudicelli et al. | 424/250 |
| 4,044,132 | 8/1977 | Najer et al. | 424/250 |

*Primary Examiner*—Stanley J. Friedman
*Attorney, Agent, or Firm*—Stevens, Davis, Miller & Mosher

[57] ABSTRACT

Anxiety or depression is treated by administering to a patient suffering from anxiety or depression an effective dosage of a piperazine of the formula

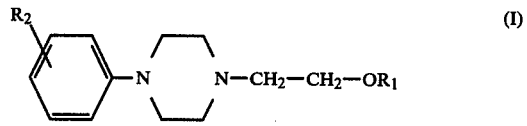

wherein
$R_1$ is hydrogen, —CO(lower alkyl) —CO(monocyclic aryl)—CONH(lower alkyl), —CON(lower alkyl)$_2$ or —CONH—(monocyclic aryl); and
$R_2$ is hydrogen, halogen, trifluoromethyl, trifluoromethylthio or trifluoromethoxy or a pharmaceutically acceptable acid addition salt thereof.

7 Claims, No Drawings

METHOD OF TREATING ANXIETY AND DEPRESSION

The present invention provides a method of treating anxiety and depression in a patient through administering to the patient an effective amount of a piperazine of the formula:

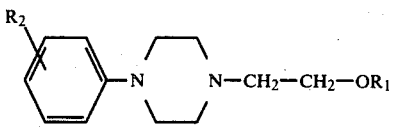

wherein
$R_1$ is hydrogen, —CO(lower alkyl) —CO(monocyclic aryl)—COHN(lower alkyl), —CON(lower alkyl)$_2$ or —COHN—(monocyclic aryl); and
$R_2$ is hydrogen, halogen, trifluoromethyl, trifluoromethylthio or trifluoromethoxy
or a pharmaceutically acceptable acid addition salt thereof.

In a preferred embodiment, the piperazine is administered in the form of a pharmaceutically acceptable acid addition salt. The monohydrochloride form of the piperazine (I) is particularly preferred.

In the definition of the piperazines (I), lower alkyl is preferably an alkyl group of up to 4 carbon atoms, such as methyl, ethyl, n-propyl, iso-propyl, n-butyl, sec-butyl and tert-butyl. As monocyclic aryl may preferably be mentioned radicals of the formula:

wherein each of $R_3$ and $R_4$ is independently hydrogen, halogen, methoxy or unsubstituted amino.

Synthesis of the piperazines may commence with the treatment of an intermediate piperazine of the formula:

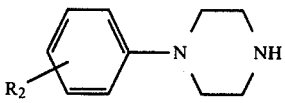

wherein $R_2$ is as hereinbefore defined, with a halogenated alcohol of formula X—CH$_2$—$_{CH2}$OH or with ethylene oxide, wherein X is halogen, to yield the piperazine (I) wherein $R_1$ is hydrogen. To produce a piperazine (I) wherein $R_1$ is other than hydrogen, the following reaction sequence may be utilized, beginning with the piperazine (I) wherein $R_1$ is hydrogen. An acid of the formula $R_1$—CO$_2$H, wherein $R_1$ is as defined above or one of its functional derivatives (preferably a halide, an anhydride or an ester) is reacted, preferably under heating, with the piperazine (I) of formula

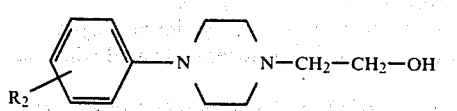

wherein $R_2$ is as defined above. For example, an acid halide, and particularly a chloride, and a compound (III) are reacted at the reflux temperature of an apolar solvent such as an aromatic hydrocarbon, e.g. benzene, toluene or xylene; or chloroform; in this case, the presence of a tertiary base which accepts the hydrogen halide acid can be advantageous. Alternatively, an acid anhydride and a compound of the formula (III), are heated at 80° C. to 150° C.; in this case, the presence of a solvent is not absolutely necessary.

The piperazines (I) of the method of the invention have been tested in the form of their hydrochlorides, with the results demonstrating the fact that the piperazines (I) are in fact anxiolytic compounds suitable for the treatment of anxiety or depression. The piperazines (I) and their pharmaceutically acceptable salts are advantageously combined with a compatible carrier so that they can be administered orally, endorectally or parenterally. For oral administration, any conventional pharmaceutical form may be used, that is to say tablets, dragees, gelatine-coated pills, capsules, cachets and drinkable solutions or suspensions, e.g. a syrup or elixir. The daily dose of the piperazine (I) is from about 15 to about 150 mg.

The following examples further illustrate the invention:

EXAMPLE I

[4-(3'-trifluoromethylthiophenyl)-piperazino]-ethanol 26.3 g (0.10 mol) of m-trifluoromethylthiophenyl-piperazine, 12.2 g (0.15 mol) of 2-chloro-ethanol, 15.9 g (0.15 mol) of sodium carbonate and 300 ml of ethanol are introduced into a flask equipped with a stirrer. After the suspension has been heated for 6 hours at the reflux temperature, the solid phase is removed by filtering the boiling reaction mixture. The ethanol is evaporated from the filtrate, the residue is taken up in diethyl ether, a slight amount of insoluble matter is filtered off, and the other solution is washed with water and dried over magnesium sulphate. The ether is driven off and the product is distilled under reduced pressure. 26.85 g (yield=87.6 percent) of [4-(3'trifluoromethylthiophenyl)-piperazino]-ethanol are thus obtained.

EXAMPLE II (4-m-trifluoromethylthiophenyl-piperazino)-ethyl acetate 2 Drops of acetyl chloride are added to 10 g (0.0326 mol) of [4-(3'-trifluoromethylthiophenyl)-piperazino]-ethanol in 60 ml of acetic anhydride and the mixture is heated at 100° for 1 hour. The excess acetic anhydride is evaporated under reduced pressure to give a residue which is dissolved in ether. The ethereal solution is washed with water and then with sodium bicarbonate solution; it is dried over anhydrous magnesium sulphate and the solvent is driven off. An oily product is obtained which is distilled under reduced pressure to give 9.55 g (yield: 84%) of [4-(3'-trifluoromethylthiophenyl)-piperazino]-ethyl acetate, which distills at 145°-150° C. under a pressure of 0.01 mm of mercury.

The monohydrochloride is prepared by dissolving 9.55 g (0.0274 mol) of the above base in 70 ml of 2-propanol and adding 6.85 ml of 4N-hydrogen chloride in ethanol. The salt formed is filtered off and dried in vacuo to give 8.5 g (yield: 80.4%) of (4-m-trifluoromethylthiophenyl-piperazino)-ethyl acetate monohydrochloride.

EXAMPLES III-XX

The piperazines (I) of the method of the invention have been demonstrated to be anxiolytic agents. This activity has been tested by the 4 plates test (Aron C. Theses de Medecine—Paris 1970; Boissier JR—Simon P. and Aron C., A new method for rapid screening of minor tranquillizers in mice, Europ. J. Pharmacol. 1968, 4, 145-151). The substances are administered in several doses (0.3, 1.0, 3.0, 10 and 30 mg/kg) per os, 60 minutes before the test.

The results, which give the percentage of desinibition observed in the mouse, are shown as Examples III-XVIII. At the same doses, the greater the percentage the higher the activity of the piperazine. The results for two known anxiolytic agents are set forth in Examples XIX and XX.

$R_1$ is hydrogen or —CO(lower alkyl); and
$R_2$ is hydrogen, halogen, trifluoromethyl or trifluoromethylthio
or a pharmaceutically acceptable acid addition salt thereof.

2. A method of treating anxiety or depression which comprises administering to a patient suffering from anxiety or depression an effective dosage of a piperazine to relieve said anxiety or depression, said piperazine having the formula:

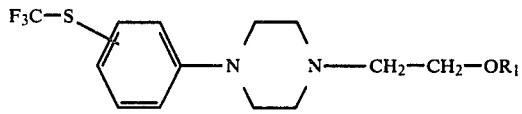

wherein
$R_1$ is hydrogen, —CO(lower alkyl), —CO(monocy-

| PIPERAZINES* (I) | | LD 50 TOXICITY | ACTIVITY mg/kg p.o. | | | | |
|---|---|---|---|---|---|---|---|
| EXAMPLE $R_1$ | $R_2$ | (mg/kg p.o.) | 0.3 | 1 | 3 | 10 | 30 |
| 3 H | 3-SCF$_3$ | 500 | +118 | +190 | +230 | +335 | +248 |
| 4 H | 3-CF$_3$ | 740 | — | — | — | +174 | +226 |
| 5 H | 3-CF$_3$O | 575 | — | +8 | +9 | +14 | +88 |
| 6 H | 3-Cl | 750 | — | +23 | +50 | +54 | — |
| 7 H | H | 525 | — | +39 | +2 | — | — |
| 8 COCH$_3$ | 3-SCF$_3$ | 510 | +27 | +88 | +191 | +312 | +154 |
| 9 COCH$_3$ | 3-CF$_3$ | 925 | — | +24 | +49 | +220 | +156 |
| 10 CO—Ph | 3-CF$_3$ | — | — | — | — | — | — |
| 11 CO—Ph(NH$_2$) | 3-CF$_3$ | 3000 | — | +35 | +63 | +182 | +336 |
| 12 CO—Ph(Cl)(OCH$_3$) | 3-CF$_3$ | 1800 | — | — | — | +65 | — |
| 13 CONHCH$_3$ | 3-SCF$_3$ | — | — | — | +49 | +152 | — |
| 14 CON(CH$_3$)$_2$ | 3-SCF$_3$ | — | — | +2 | — | +3 | — |
| 15 CONHC$_4$H$_9$ | 3-SCF$_3$ | — | — | +3 | +109 | +64 | — |
| 16 CONHC$_4$H$_9$ | 3-CF$_3$ | — | — | — | — | — | — |
| 17 CONH—Ph | 3-CF$_3$ | — | — | — | — | +9 | +30 |
| 18 CONH—Ph | 3-SCF$_3$ | — | +15 | +23 | +63 | +304 | +532 |
| 19 meprobamate | | — | — | — | +53 | +38 | +142 |
| 20 chlordiazepoxide | | — | — | +43 | +86 | +24 | — |
| 21 CO—C(CH$_3$)$_3$ | 3-SCF$_3$ | — | — | +73 | +122 | +196 | — |

What is claimed is:

1. A method of treating anxiety or depression which comprises administering to a patient suffering from anxiety or depression an effective dosage of a piperazine to relieve said anxiety or depression, said piperazine having the formula:

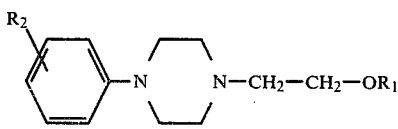

wherein clic aryl), —CONH(lower alkyl), —CON(lower alkyl)$_2$ or —CONH(monocyclic aryl)
or a pharmaceutically acceptable acid addition salt thereof.

3. A method of claim 2 wherein said piperazine is [4-(3'-trifluoromethylthiophenyl)-piperazino]-ethanol or a pharmaceutically acceptable salt thereof.

4. A method of claim 3 wherein said piperazine is in the form of its hydrochloride.

5. A method of claim 2 wherein said piperazine is [4-(3'-trifluoromethylthiophenyl)-piperazino]-ethyl acetate or a pharmaceutically acceptable acid addition salt thereof.

6. A method of claim 5 wherein said piperazine is in the form of its hydrochloride.

7. A method of treating anxiety or depression which comprises administering to a patient suffering from anxiety or depression an effective dosage of a piperazine to relieve said anxiety or depression, said piperazine having the formula:

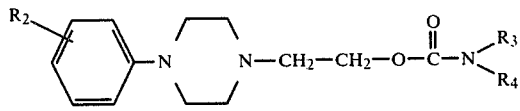

wherein
$NR_3R_4$ is —NH(lower alkyl), —N(lower alkyl)$_2$ or —NH(monocyclic aryl), and
$R_2$ is hydrogen, halogen or trifluoromethyl, or a pharmaceutically acceptable acid addition salt thereof.

* * * * *